US00PP27647P3

(12) United States Plant Patent
Farrow

(10) Patent No.: US PP27,647 P3
(45) Date of Patent: Feb. 7, 2017

(54) ***BUXUS* PLANT NAMED 'MONALEX'**

(50) Latin Name: *Buxus sempervirens*
Varietal Denomination: MonAlex

(71) Applicant: Michael Farrow, Warwick, MD (US)

(72) Inventor: Michael Farrow, Warwick, MD (US)

(73) Assignee: Monrovia Nursery Co., Azusa, CA (US)

( * ) Notice: Subject to any disclaimer, the term of this patent is extended or adjusted under 35 U.S.C. 154(b) by 62 days.

(21) Appl. No.: 14/545,505

(22) Filed: May 12, 2015

(65) Prior Publication Data

US 2016/0338236 P1 Nov. 17, 2016

(51) Int. Cl.
*A01H 5/12* (2006.01)

(52) U.S. Cl.
USPC ..... Plt./226

(58) Field of Classification Search
USPC ..... Plt./226
See application file for complete search history.

*Primary Examiner* — Anne Grunberg
(74) *Attorney, Agent, or Firm* — Cassandra Bright

(57) ABSTRACT

A new and distinct *Buxus* cultivar named 'MonAlex' is disclosed, characterized by a distinctive conical growth habit. Plants grow slowly, have bright green foliage and exhibit improved resistance to diseases of *Buxus*. The new cultivar is a *Buxus*, suitable for ornamental garden purposes.

1 Drawing Sheet

Latin name of the genus and species: *Buxus sempervirens*.
Variety denomination: 'MonAlex'.

BACKGROUND OF THE INVENTION

The new cultivar is a product of chance discovery by the inventor. This new variety, hereinafter referred to as 'MonAlex', was discovered as a naturally occurring, whole plant mutation by the inventor, Michael Farrow. The interesting new mutation was discovered in a private garden in Earleville, Md. among plants of unpatented *Buxus sempervirens* during Summer of 2006.

After identifying the new variety as a potentially interesting selection, the inventor first organized propagation of 'MonAlex' by vegetative cuttings at a commercial nursery in Dayton, Oreg. October of 2009. The inventor continued controlled testing and propagation, assessing stability of the unique characteristics of this variety. At least three generations have been reproduced and have shown that the unique features of this cultivar are stable and reproduced true to type.

SUMMARY OF THE INVENTION

The cultivar 'MonAlex' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MonAlex' These characteristics in combination distinguish 'MonAlex' as a new and distinct *Buxus* cultivar:

1. Very slow growth.
2. Distinctive conical growth habit.
3. Higher resistance to disease.
4. Bright green foliage.

COMPARISON TO PARENT VARIETY

'MonAlex' is similar in most horticultural characteristics to the parent variety. Plants of the new cultivar 'MonAlex' however have a conical growth habit not exhibited by the parent variety. Additionally, the parent variety does not exhibit the disease resistance found with 'MonAlex'.

COMMERCIAL COMPARISON

'MonAlex' is similar in most horticultural characteristics to the unpatented commercial variety *Buxus sempervirens* 'Vardar Valley'. Plants of the new cultivar 'MonAlex' however have a conical growth habit not exhibited by this comparator. Additionally, the new variety has a brighter green foliage color

BRIEF DESCRIPTION OF THE PHOTOGRAPHS

The accompanying photograph in FIG. 1 illustrates in full color a typical plant of 'MonAlex' grown outdoors in Dayton, Oreg. The plant is approximately 2 years old, and is shown in a three gallon container, exhibiting typical conical growth. The plant photographed has not been pruned and naturally grows as pictured.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MonAlex' plants grown outdoors in Dayton, Oreg. Plants are approximately 2 years old, in a 3 gallon nursery container. Measurements and numerical values represent averages of typical plant types.

Botanical classification: *Buxus sempervirens* 'MonAlex'.

PROPAGATION

Time to rooting: About 10 to 14 days at 25° C. to 30° C.
Time to produce a rooted young plant: About 45 to 60 days at 25° C. to 30° C.
Root description: Fibrous, very well branched. Colored near RHS Brown 199B, 199C.

PLANT

Growth habit: Conical, uniform appearance.
Height: Approximately 50 cm. after 2 years.
Plant spread: Approximately 35 cm at widest point.
Typical growth rate: Slow for species.
Branching characteristics: Very dense branches. No single central stem. Approximately 20 central upright branches, each of these with dense opposite branching occurring at an internode length between 1.5 to 3.5 cm. Lateral stems are held at an angle of approximately 15 degree from the central branch.
Length of lateral branches: Average range 5 to 11 cm.
Diameter of lateral branches: Approximately 0.5 cm.
Lateral branch shape in cross section: Generally round.
Lateral branch strength: Very strong, not easily broken.
Lateral branch color:
*Young*.—Near Green 143C.
*Mature*.—Near RHS Green 143 C covered in Grey-Brown 199C scales.
Lateral branch texture: Scaly and rough.
Internode length: Average range 1.5 to 3.5 cm.
Lenticels present: No.

FOLIAGE

Leaf:
*Arrangement*.—Opposite.
*Type*.—Simple.
*Shape of blade*.—Obovate.
*Average length*.—Approximately 1.8 cm.
*Average width*.—Approximately 1.1 cm.
*Apex*.—Young foliage emarginate. Mature foliage mucronate.
*Base*.—Rounded.
*Attachment*.—Petiolate.
*Margin*.—Entire.
*Texture of top surface*.—Glabrous.
*Texture of bottom surface*.—Glabrous.
*Appearance of top surface*.—Very glossy.
*Appearance of bottom surface*.—Very slightly glossy.
*Leaf internode length*.—Average 1.0 cm.
*Color*.—Young foliage upper side: A color between RHS Green 143A and 138A. Young foliage under side: Near RHS Yellow-Green 144A. Mature foliage upper side: A bright green color, closest description with RHS a color between yellow-Green 144A and Green 137A. Mature foliage under side: Near RHS Yellow-Green 144A.
*Venation*.—Type: Pinnate. Venation color upper side: Near RHS Yellow-Green 144A. Venation color under side: Near RHS Yellow-Green 144B. Prominent mid vein color near Yellow-Green 145C.
*Durability of foliage to stresses*.—Flexible and resistant to breakage.
*Fragrance*.—Faint to no foliage scent.
Petiole:
*Length*.—Average 0.15 cm.
*Diameter*.—0.1 cm.
*Pubescence*.—None, all surfaces glabrous.
*Color*.—Upper Surface near RHS Yellow-Green N144B. Lower Surface Near RHS Yellow-Green 144A.

FLOWER

Flowering not observed.

OTHER CHARACTERISTICS

Disease and pest resistance: Greater resistance to normal diseases of *Buxus* has been observed. Neither resistance nor susceptibility to pests has been observed.
Drought tolerance: No tolerance for drought.
Temperature tolerance: USDA Zones 5-9.

What is claimed is:

1. A new and distinct cultivar of *Buxus* plant named 'MonAlex' as herein illustrated and described.

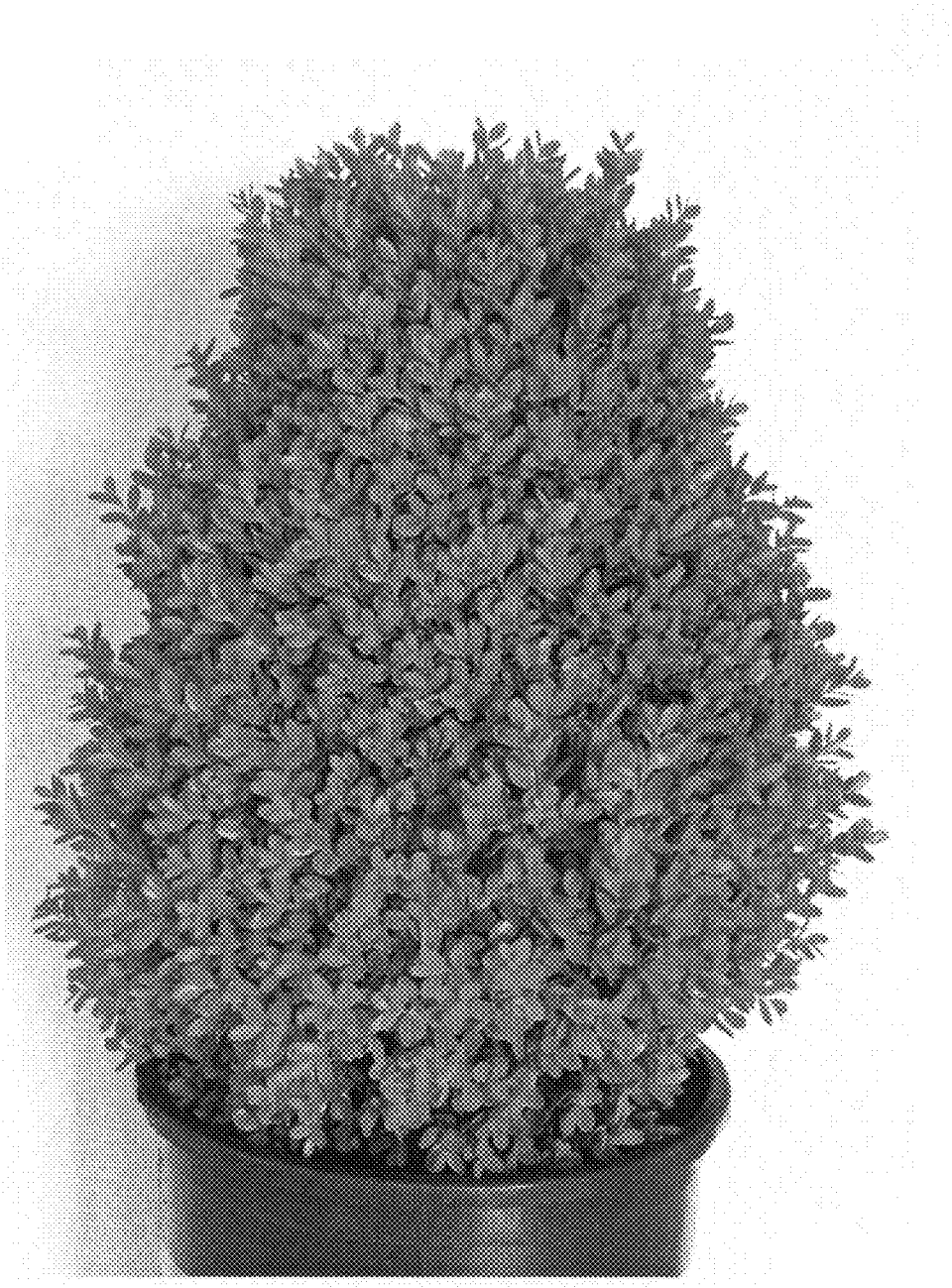

* * * * *